United States Patent
Shepodd et al.

(10) Patent No.: US 7,488,407 B2
(45) Date of Patent: Feb. 10, 2009

(54) CASTABLE THREE-DIMENSIONAL STATIONARY PHASE FOR ELECTRIC FIELD-DRIVEN APPLICATIONS

(75) Inventors: Timothy J. Shepodd, Livermore, CA (US); Leroy Whinnery, Jr., Danville, CA (US); William R. Even, Jr., Livermore, CA (US)

(73) Assignee: Sandia Corporation, Livermore, CA (US)

( * ) Notice: Subject to any disclaimer, the term of this patent is extended or adjusted under 35 U.S.C. 154(b) by 892 days.

(21) Appl. No.: 10/969,134

(22) Filed: Oct. 19, 2004

(65) Prior Publication Data

US 2005/0051430 A1    Mar. 10, 2005

Related U.S. Application Data

(60) Division of application No. 09/796,762, filed on Feb. 28, 2001, now Pat. No. 6,846,399, which is a continuation-in-part of application No. 09/310,465, filed on May 12, 1999, now abandoned.

(51) Int. Cl.
    *F04F 11/00* (2006.01)
(52) U.S. Cl. ...................... 204/600; 204/450
(58) Field of Classification Search ........... 204/600, 204/601, 605, 450, 451, 455
    See application file for complete search history.

(56) References Cited

U.S. PATENT DOCUMENTS

| 6,117,326 A * | 9/2000 | Schure et al. ........... 210/635 |
| 2001/0008212 A1 * | 7/2001 | Shepodd et al. ......... 204/451 |

OTHER PUBLICATIONS

Peters et al, Analytical Chemistry 1997, 69, pp. 3646-3649.*
CAS Registry entry for 2-Propenoic acid, 2-methyl-, 1,1'-(1,2-ethanediyl) ester, 2008.*

* cited by examiner

*Primary Examiner*—Kaj K Olsen
(74) *Attorney, Agent, or Firm*—Donald A. Nissen

(57) ABSTRACT

A polymer material useful as the porous dielectric medium for microfluidic devices generally and electrokinetic pumps in particular. The polymer material is produced from an inverse (water-in-oil) emulsion that creates a 3-dimensional network characterized by small pores and high internal volume, characteristics that are particularly desirable for the dielectric medium for electrokinetic pumps. Further, the material can be cast-to-shape inside a microchannel. The use of bifunctional monomers provides for charge density within the polymer structure sufficient to support electroosmotic flow. The 3-dimensional polymeric material can also be covalently bound to the channel walls thereby making it suitable for high-pressure applications.

1 Claim, 1 Drawing Sheet

US 7,488,407 B2

CASTABLE THREE-DIMENSIONAL STATIONARY PHASE FOR ELECTRIC FIELD-DRIVEN APPLICATIONS

CROSS-REFERENCE TO RELATED APPLICATIONS

This application is a division of prior application Ser. No. 09/796,762 filed Feb. 28, 2001 (now U.S. Pat. No. 6,846,399) which is a Continuation-in-Part of prior application Ser. No. 09/310,465 filed May 12, 1999 now abandoned.

STATEMENT OF GOVERNMENT INTEREST

This invention was made with Government support under contract no. DE-AC04-94AL85000 awarded by the U.S. Department of Energy to Sandia Corporation. The Government has certain rights in the invention.

BACKGROUND OF THE INVENTION

This invention is directed generally to microfluidic devices that employ electroosmotic flow, and particularly electrokinetic pumps, having flow channels that contain a stationary phase or porous dielectric material prepared by an inverse emulsion method that imparts desirable structure and properties.

Monolithic polymeric materials composed of polymerized monomers (styrenes, acrylates, methacrylates, etc.) have proven useful as the stationary phase for various chromatographic applications and particularly for applications involving miniaturized or capillary columns where traditional methods of column packing have proven to be ineffective. Polymer materials are among the class of materials that have been found to be useful for electric field-driven applications and particularly as porous dielectric media for electrokinetic pump applications. Porous stationary phase materials that are "cast-in-place" or "cast-to-shape" by phase-separation polymerization of mixtures of monomers directly within the confines of a chromatographic column, such as those disclosed in U.S. Pat. No. 5,728,457 entitled "Porous Polymer Material with Gradients" and issued to Frechet et al. on Mar. 7, 1998, have been developed to address this problem. By careful control of polymerization rate, time, and temperature Frechet has produced a single molded polymer monolith that possesses desirable hydrodynamic properties by virtue of being traversed by large channels and permeated by small pores. Several variations have already been successfully used in the separation of polyaromatic hydrocarbons (PAH), PTH-labeled amino acids, peptides, and explosives.

In phase-separation polymerization, a solution of monomers is polymerized. When the polymer molecules grow sufficiently large, they separate from the inert solvent (phase separate). A liquid-liquid or liquid-solid phase separation can occur with partitioning of the unreacted monomers. If a three-dimensional network is formed before precipitation, a polymer monolith consisting of a three-dimensional network of solid polymer and an interconnected network of solvent filled pores will be formed. The structure and dimensions of the interconnected porous polymer network can generally be determined by controlling the proportions of solvent as well as the monomer and solvent composition. However, prior art phase separation processes for producing polymer stationary phase material are very difficult to control completely since the polymer microstructure is determined principally, and irreversibly, by the conditions that prevail at the time of phase separation. Thus, if the desired network structure has not formed, the polymer can precipitate as a particulate material. Further, an undesired structure cast by prior art phase-separation methods into an intricate substrate either cannot be removed or can only be removed with great difficulty, generally requiring the substrate to be completely refabricated.

SUMMARY OF THE INVENTION

The present invention is directed to microfluidic devices, and particularly to electrokinetic pumps, that employ electroosmotic flow and, are characterized generally by having at least one fluid flow channel that contains a stationary phase or porous dielectric material. As described herein, the stationary phase or porous dielectric material comprises a robust polymeric material, prepared by an inverse emulsion polymerization method, that has an internal structure that provides a high strength stationary phase. In addition, problems associated with the production of cast-to-shape polymeric stationary phase materials in microchannels and removal of solvents are solved.

In contrast to prior art phase separation polymerization processes, an inverse emulsion polymerization process provides an easily controllable method for producing a polymer material having characteristics that are particularly desirable for stationary phase materials for electric field-driven applications and, in particular, as the dielectric medium for electrokinetic pumps. The polymer material comprising a 3-dimensional polymer network characterized by small pores and high internal volume, can also be used as a passive mechanical support structure, wherein a low viscosity monomer can be diffused into the porous structure to provide a dielectric material for electrokinetic pump applications. The use of bifunctional monomers provides a plurality of charged sites within the polymer structure, thereby making this material suitable as the stationary phase for applications using electroosmotic flow particularly in non-silica columns, and for binding the 3-dimensional polymeric material to the walls of the microchannels, thereby making it suitable for high pressure applications, such as could be encountered in electrokinetic pump applications. Moreover, since the aqueous phase that forms the structure of the inverse emulsion is conductive it can be easily exchanged for other aqueous phases using electroosmotic flow, thereby eliminating the need for high pressure pumping. The inventive polymer material has also been shown to be stable over a pH range of 1-12.

DETAILED DESCRIPTION OF THE INVENTION

Figure 1:
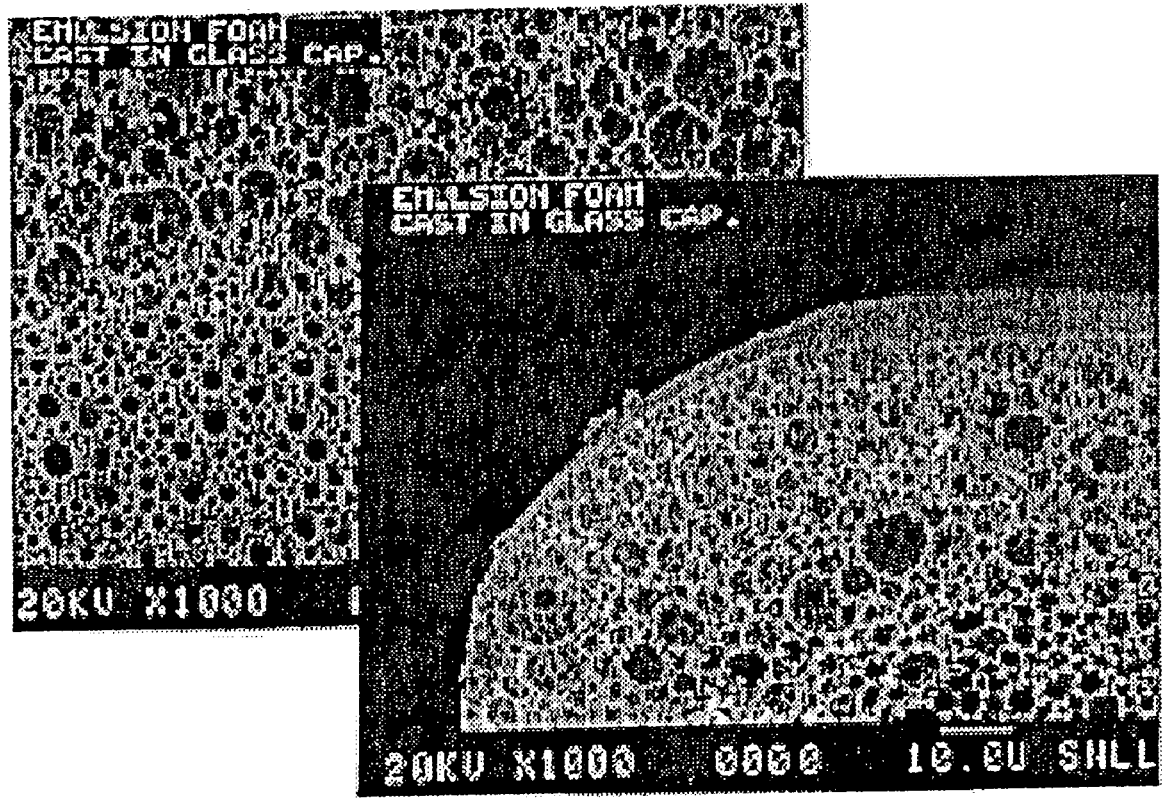
FIG. 1 shows the 3-dimensional, interconnected microstructure of an inverse emulsion polymer material.

The present invention is directed to microfluid devices that employ electroosmotic flow for applications such as capillary electrochromatography and capillary zone electrophoresis, and particularly electrokinetic pumping and thus, have at least one fluid flow channel that has a stationary phase or porous dielectric material disposed therein. In this invention, that material comprises a 3-dimensional polymer material that can be cast-to-shape inside a capillary tube, microchannel, or a micromachined groove to form a material that possesses unique features that makes it especially suitable as a stationary phase for these electric field-driven applications. Included among these features are: 1) an interconnected 3-dimensional network of organic struts that provide a high internal volume and surface area and can also act as a framework for infusion of a low viscosity monomer that can be subsequently polymerized in place to support electroosmotic flow (see FIG. 1); 2) a surface that can contain charged groups that support electroosmotic flow, as discussed above; and 3) the ability to bond to the walls of the chromatographic column. The porous polymeric material produced by the inverse emulsion method described herein can comprise a random copolymer having the following generic formula

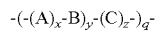

wherein, A, B, and C can be monovinyl, polyvinyl, and bifunctional monomers, respectively, and x, y, and z are greater than or equal 0 and can be equal or unequal to each other and q is greater than zero. A preferred embodiment of the generic polymeric material is given by the following structural formula

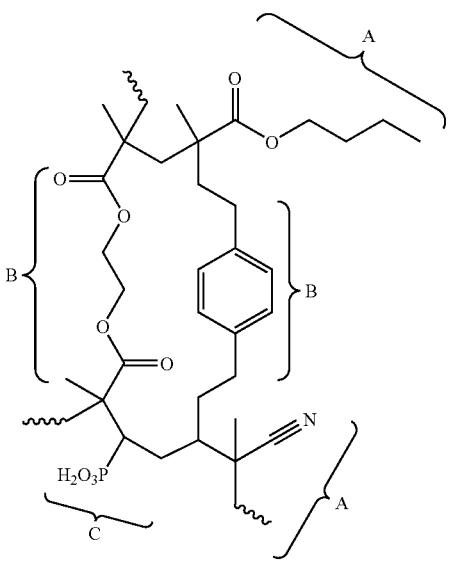

While the invention will be described and illustrated in relation to microchannels and arrangements thereof it is understood that the microchannels themselves are part of a microfluidic device. The microfluidic device can be comprised of channels, reservoirs, and arbitrarily shaped cavities that are fabricated using any of a number of art recognized microfabrication methods, including injection molding, hot embossing, wet or dry etching, or deposition over a sacrificial layer. The microfluidic device can also include holes and/or ports and/or connectors to adapt the microfluidic channels and reservoirs to external fluid handling devices. The terms "channel, microchannel, capillary, or capillary channel" as used herein refers to enclosed structures that are generally fabricated on the micron or submicron scale, i.e., having at least one cross-sectional dimension in the range from about 0.1 µm to about 500 µm.

Applying an electric potential between the electrodes in contact with the electrolyte will cause the electrolyte to move in the microchannel by electroosmotic flow and a pressure differential can be created along the length of the porous dielectric medium. Consequently, it is desirable to provide the dielectric medium with functionality that will bind the dielectric medium to the walls of the microchannel fixing it in place. Additionally, it is desirable that the microstructure of the porous dielectric medium be strong enough to withstand such pressures without collapse.

Electric field-driven flow, and particularly electroosmotic flow, can be used to generate high pressure and an apparatus that uses electroosmotic flow to provide a high pressure hydraulic system for pumping and/or compressing fluids has been developed, as disclosed in U.S. Pat. No. 6,013,164 issued Jan. 11, 2000 to Paul and Rakestraw, incorporated herein by reference. An electrokinetic pump (EKP) apparatus consists generally of at least one tube or channel, that can be a capillary channel or microchannel, forming a fluid passageway containing an electrolyte and having a porous dielectric medium capable of supporting electroosmotic flow disposed therein between one or more pairs of spaced electrodes.

The surface of a solid can become charged through adsorption of ions from solution causing an electrically charged layer (electric double layer) to exist at the solid/liquid interface. Surface charge on a solid can also arise by virtue of the nature of the surface of the solid, i.e., the surface inherently contains charged species, The application of electrodes to the solid to produce an in-situ electric field results in the displacement of the mobile charged layer in the liquid with respect to the stationary charged surface layer. The solid phase being fixed while the liquid is free to move, the liquid will tend to flow or be pumped through the pores of the solid phase. The direction the liquid moves is dependent upon the sign of the charge it carries with respect to that of the solid and the velocity with which the liquid moves has been shown to be dependent upon the magnitude of the electric field. A silica-based porous dielectric medium has a negative surface charge and thus the electrolyte will flow toward the more negative electrode potential. On the other hand, by using a material for the porous dielectric medium that has a positive surface charge, such as alumina, the electrolyte can be made to flow toward the more positive electrode potential.

Polymer material produced by an inverse emulsion polymerization process, such as that disclosed herein, can be employed in electric field-driven or electroosmotic flow applications, such as an EKP, wherein the polymer can act as the porous dielectric medium itself because of incorporated charged groups or as a high strength support medium that can provide a framework for deposition of a polymer material that contains the charged groups necessary for electroosmotic flow. Furthermore, the structure produced by inverse emulsion polymerization methods acts to compartmentalize an EKP dielectric medium into many small individual pumps that act synergistically as one large EKP. Moreover, this dielectric medium is no longer subject to catastrophic failure due to cracking from repeated pressure cycling or thermal stresses since physical failures of the inverse emulsion medium is localized in the individual cells that make up the network of the polymer medium. The inventors have shown that it is possible to generate pressures as high as 4200 psi by the application of 5 kV between the spaced electrodes using an acetonitrile electrolyte and a dielectric material composed of a 3-dimensional polymer material made by an inverse emulsion as described herein.

An inverse emulsion (water-in-oil) can be used to prepare the polymer material that can serve as a stationary phase or porous dielectric material for electroosmotic force-driven applications. The term "oil" is a generic term signifying the organic phase that when mixed with water forms the oil-in-water emulsion. The formulation of a water-in-oil emulsion is straightforward. A surfactant of low polarity is mixed with the emulsion such that the nearly spherical droplets of water are coated in surfactants and the interstices between the droplets are filled with the oil (organic) phase. A thermally labile free-radical initiator is used to initiate the radical chain reactions that lead to polymerization. Upon polymerization, the monomeric material that comprises the oil phase surrounding the aqueous droplets becomes a monolithic structure that provides the 3-dimensional network shown in FIG. 1. A variety of monomers can be used. Any oil soluble or even partitioned monomer is useful as part of the monolith.

The following illustrates generally an inverse emulsion process for preparing a polymer structure that can be used as a stationary phase material in electric field-driven applications and as the porous dielectric material in an EKP. A continuous organic phase made up of monomers and a cross-linking agent such as divinylbenzene is mixed together with a surfactant such as sorbitan monoleate and water to form an emulsion; the aqueous phase, that can include an initiator, serves as a temporary pore forming phase. The character of the emulsion can be appropriately modified by the use of co-solvents, solutes, and salts to vary the ionic strength. Further, as discussed above suitable bifunctional monomers can be added to the organic phase to provide a charged polymer structure disposed in a channel across its internal cross-sectional area and/or covalent linkage to the column walls.

The aqueous phase can contain ionic strength modifiers, such as ammonium chloride and/or magnesium sulfate, and including a surfactant that is dispersed in the pre-polymer organic phase by emulsification. The term pre-polymer means a pre-polymerized group of monomers that can be chain extended by condensation reaction to form a polymeric material. The organic phase can contain monovinyl monomers, or polyvinyl monomers or mixtures thereof. Suitable monovinyl monomers include, but are not limited to, styrene, methacrylonitrile, various acrylates, and methacrylates. Polyvinyl monomers are employed as crosslinking agents. Suitable polyvinyl monomers include, but are not limited to, divinylbenzene, ethylene glycol dimethylacrylate, and trimethylolpropane trimethylacrylate. All monomers used should polymerize readily below 100° C. because boiling the aqueous phase will typically break the emulsion. Thermal or optical polymerization initiators common to the art such as peroxides, persulfates, or azo compounds can be used to accelerate polymerization and support electroosmotic flow applications. The organic phase can further contain bifunctional monomers such as trialkoxysilyl-functionalized monomers and particularly trimethyloxysilylpropylmethacrylate that can provide a covalent link to the walls of silica capillary columns. These bifunctional monomers can further provide charged sites to support electroosmotic flow and can be selected from the group consisting of sulfonates, phosphonates, boronates, and alkyl ammonium and ammonium compounds containing active vinyl groups in the molecule. Particularly preferred are sodium vinyl sulfonate, vinyl phosphonic acid, and 4-vinyl phenylboronic acid. Moreover, by incorporating acidic or basic functionalities, particularly vinyl pyridine that provides a basic moiety that can be protonated to pyridinium at low pH, it is possible to adjust the direction of electroosmotic flow.

The use of persulfate initiators is particularly desirable since they can be incorporated into the polymer at sufficient levels (typically about 0.5%) to support electroosmotic flow in a mixture of otherwise neutral monomers. In addition, as persulfate decomposes and forms hydrogen sulfate, the pH drops. Acidification of the aqueous phase produces rapid hydrolysis of coupling agents, such as trimethoxysilyl, during polymerization after the emulsion is injected into the capillary, and binds the polymer to the walls of the capillary or microchannel.

After the emulsion has been formed and cast into the microchannel or capillary the organic phase is polymerized into a monolithic structure by initiating polymerization, either thermally or optically, and thereby permanently fixing the 3-dimensional structure of the emulsion in place. The microstructure of the polymer having been determined and fixed by the emulsification conditions.

A stationary phase or porous dielectric material can be produced by an inverse emulsion process and the desired 3-dimensional network can be established or developed prior to polymerizing the monomer components of the emulsion. Thus, the 3-dimensional structure of this polymer material is not subject to the vagaries of a phase separation process, the polymer product faithfully retains the microstructure of the emulsion. Thus, if the microstructure of the emulsion is not that desired the emulsification process can be modified, the emulsion re-emulsified, or a new batch prepared. This advantage contrasts with prior art phase separation processes for producing polymer stationary phase material where the polymer microstructure is determined principally, and irreversibly, by the conditions that prevail at the time of phase separation that are very difficult to control completely. The microstructure of the prior art phase separated material is determined only after irreversible phase separation has occurred during the polymerization process and not prior to polymerization as in the present invention. By providing for determination of the microstructure of the polymer stationary phase prior to the step of polymerization, an inverse emulsion polymerization process such as that described herein offers further advantage in that undesirable emulsion structures can be easily forced or rinsed out of substrates having complex geometries and multidimensional arrays, allowing additional attempts to cast a polymer material having the desired structure without damaging or altering the substrate. Moreover, the inverse emulsions prepared by the methods set forth herein are quite stable they can be introduced into capillaries and other micromachined structures under pressure or by vacuum.

Following casting or pressure injection of the emulsion, the organic phase can be polymerized thermally, by heating to a temperature of less than 100° C., or by optical initiation. As described above, the 3-dimensional polymer structure can be permanently fixed into a microchannel or micromachined groove by acid hydrolysis of the coupling agent contained in the emulsion mixture. Once fixed in place, the aqueous phase, which formed the structure of the inverse emulsion, can be exchanged for an aqueous phase whose composition can be the same or different, a nonaqueous phase, or mixtures thereof by the use of pressure or preferably, because this phase is conductive, by the electroosmotic force produced by the application of an electric field to the contents of the microchannel.

An aspect of the present invention will now be illustrated by reference to a preferred embodiment that is incorporated into and forms part of this invention. This embodiment only serves to illustrate one method of forming a porous dielectric medium suitable for use in an EKP and is not intended to be limiting. Modifications and variations may become apparent to those skilled in the art, however, it is intended that these modifications and variations come within the scope of the appended claims and the invention be limited only by the scope and content of the claims.

A polypropylene container having a hole in its side plugged with a rubber septum, was evacuated to a pressure of less than about 1 Torr and secured in a paint shaker-type mixer. About 0.7 ml of a mixture of styrene, divinylbenzene and vinyl pyridine in the weight ratio of 5:1:1 was injected through the septum into the evacuated container. Next, about 0.4 g of the surfactant sorbitan monooleate was added. Monomer and solvent represent about 11 wt % of the emulsion. The remaining 89 wt % of the emulsion, comprising pore forming aqueous solution containing about 2 wt % magnesium sulfate, and 1 wt % persulfate was slowly added in small aliquots; the mixer was run for a brief period of time between additions. After all the aqueous solution had been added, the mixer was run for about 5-10 minutes to complete forming the emulsion. The emulsion, which was white and had a high viscosity, could be injected, or drawn by vacuum, directly into a chromatographic column or a micromachined groove. Aging the inverse emulsion in a 65° C. oven overnight effected complete polymerization. A photomicrograph of the structure of the material prepared by the method set forth above is shown in FIG. 1.

We claim:

1. A microfluidic device comprising an enclosed channel having a polymer disposed therein, wherein the polymer has the generic formula

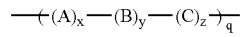

wherein, A, is selected from styrene, methacrylonitrile, acrylates, vinyl pyridine, or methacrylates, B is selected from divinylbenzene, ethylene glycol dimethylacrylate, or trimethylolpropane trimethylacrylate and C is selected from trialkoxysilyl functionalized monomers, sulfonates, phosphonates, boronates, alkyl ammonium, or ammonium compounds containing active vinyl groups, trimethyloxysilylpropylmethacrylate, sodium vinyl sulfonate, vinyl phosphonic acid, or 4 vinyl phenylboronic acid, x, y, and z are greater than zero and can be equal or unequal and q is greater than zero and;

basic functionalities, wherein said basic functionalities include vinyl pyridine or vinyl imidazole.

* * * * *